United States Patent

Hobbs et al.

[11] Patent Number: 6,059,825
[45] Date of Patent: May 9, 2000

[54] CLOT FILTER

[75] Inventors: Eamonn Hobbs, Queensbury; William Appling, Hartford, both of N.Y.

[73] Assignee: Angiodynamics, Inc., Queensbury, N.Y.

[21] Appl. No.: 08/081,984

[22] Filed: Jun. 23, 1993

Related U.S. Application Data

[63] Continuation-in-part of application No. 08/004,635, Jan. 12, 1993, abandoned, which is a continuation of application No. 07/846,142, Mar. 5, 1992, abandoned.

[51] Int. Cl.$^7$ ....................................... A61F 2/06
[52] U.S. Cl. .................... 623/1.18; 623/1.22; 623/1.3
[58] Field of Search ................................. 623/1, 11, 12, 623/901; 606/191–200, 158, 108; 604/96

[56] References Cited

U.S. PATENT DOCUMENTS 5,334,208  8/1994  Soehendra et al. ..................... 606/108

FOREIGN PATENT DOCUMENTS

| | | | |
|---|---|---|---|
| 3203410 | 11/1982 | Germany | 606/194 |
| 2238245 | 5/1991 | United Kingdom | 606/194 |

*Primary Examiner*—Mickey Yu
*Attorney, Agent, or Firm*—McAuley Nissen Goldberg Kiel & Hand, LLP

[57] ABSTRACT

A removable or absorbable vena cava filter is introducible through a relatively small bore catheter. These filters formed of a single high-memory wire. The wire has a coiled cylindrical portion and a coiled conical portion. The wire assumes a straight configuration when in a catheter. The coils of the cylindrical portion have a sufficiently large diameter contact the walls of the inferior vena cava with sufficient force to hold the coils in place against the inferior vena cava. The cylindrical portions of the wire has an anchor attached to it in a non-absorbable embodiment of the invention. The conical portion of the wire has a segment which aids in the removing of the filter from the vena cava.

13 Claims, 2 Drawing Sheets

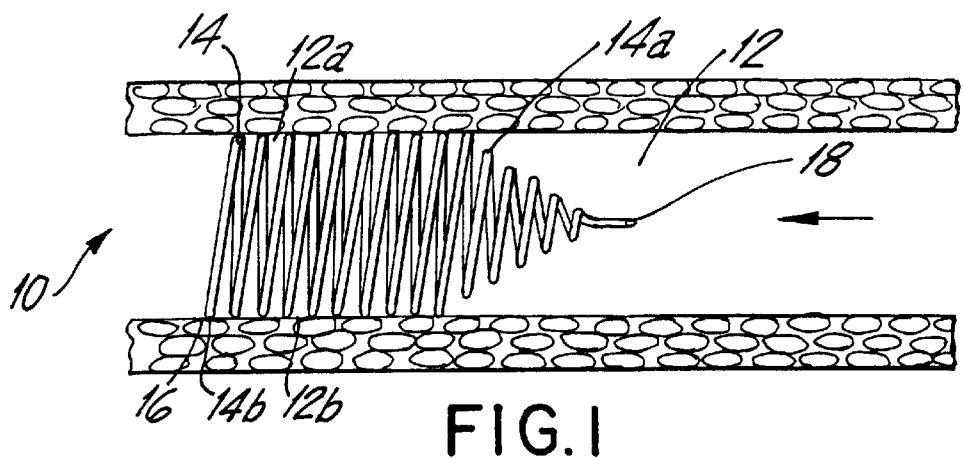
FIG.1
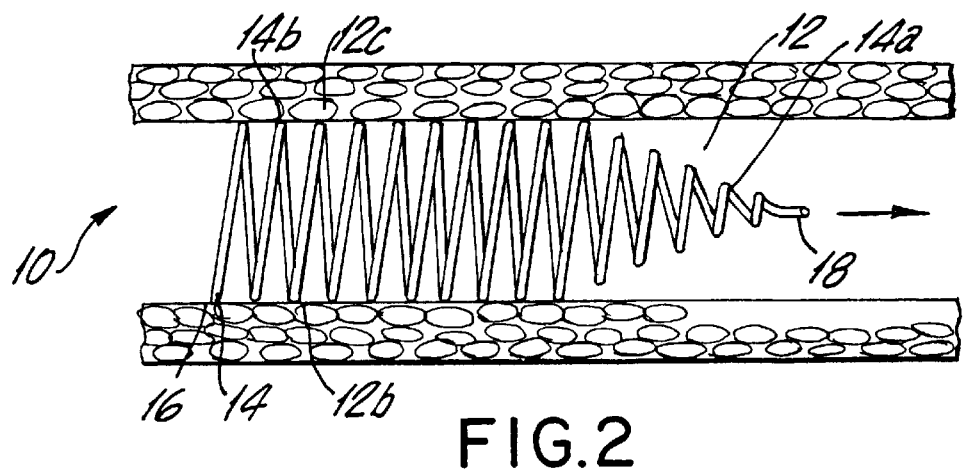
FIG.2
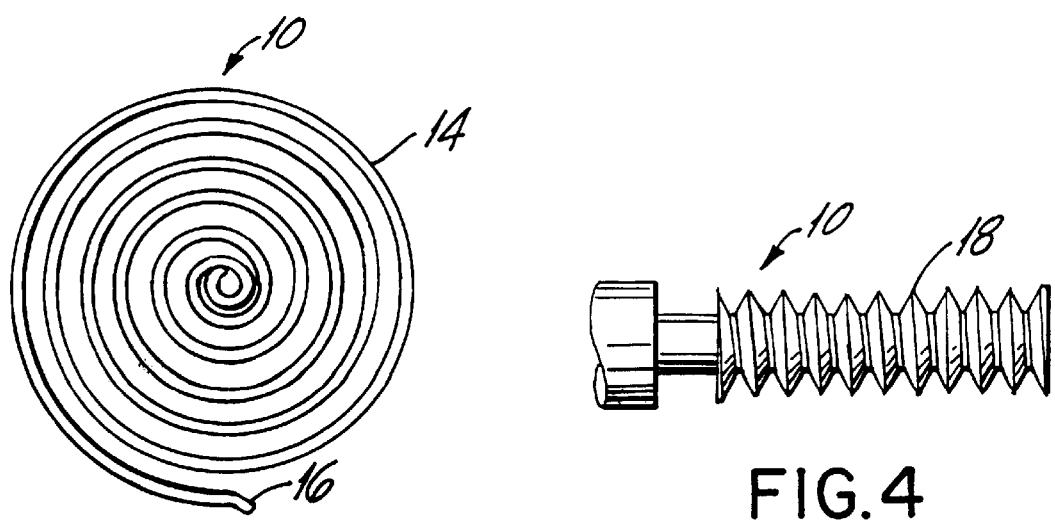
FIG.3
FIG.4

CLOT FILTER

RELATED APPLICATION

This is a Continuation-In-Part of U.S. patent application Ser. No. 08/004,635 filed on Jan. 12, 1993, abandoned, which was a Continuation of U.S. patent application Ser. No. 07/846,142 filed on Mar. 5, 1992, abandoned, both entitled Vena Cava Filter.

BACKGROUND OF THE INVENTION

The following invention relates to a clot filter and more specifically to an improved vena cava clot filter.

Vena cava clot filters are implantable devices positioned in the inferior vena cava. They are used to filter peripheral venous blood clots, which if remaining in the blood stream can migrate and cause harm. Although problems with such blood clots may not be chronic, most presently used vena cava filters are permanently implanted in the inferior vena cava and remain there for the duration of the patient's life. The filters themselves can cause clots and thus the use of a non-removable filter can be dangerous. These filters are non-removable and are generally inserted via the femoral or jugular vein.

It is preferable to be able to remove a vena cava filter and removable vena cava filters are known in the art. These removable filters must be introduced using a large bore catheter, such as an 8–14 french catheter. Such large bore catheters in a vein present dangers such as bleeding and vein dissection.

A problem with currently existing filters is that in some patients, where there is a very diffuse deep vein clot or thrombosis, large showers of clot can completely occlude the filter or force the filter out of position.

Presently known, vena cava filters are complex in design and expensive to manufacture.

Accordingly, it is an object of the present invention to provide a non-permanent vena cava filter that is introducible through a relatively small bore catheter.

Another object of the present invention to provide such a filter that will allow clots, of a certain size, to pass through the filter thereby lessening the possibility of having the filter occluded or forced out of position.

Still a further object of the present invention is to provide such a filter which is relatively simple in design and is relatively inexpensive to manufacture.

BRIEF DESCRIPTION

The present invention resides in a non-permanent vena cava filter introducible through a relatively small bore catheter. The filter is formed of a single, high memory wire. The wire has a coiled cylindrical portion and a coiled conical portion. The wire assumes a straight configuration when in a catheter. A predetermined number of the coils of the cylindrical portion have a sufficiently large diameter to contact the walls of the inferior vena cava with sufficient force to hold the coils in place against the inferior vena cava. The cylindrical portion is formed to be of sufficient length with respect to the entire filter such that its length together with the diameter of its coils act to center the filter in the vena cava. The cylindrical portion of the wire has an anchor attached to it. The wire may either be removable or absorbable. If the wire is removable, the conical portion of the wire has a segment which aids in the removing of the filter from the vena cava.

BRIEF DESCRIPTION OF THE DRAWINGS

FIG. 1 is a schematic side view, in section, of one embodiment the vena cava filter of the present invention as inserted in the vena cava.

FIG. 2 is similar to FIG. 1, but shows the filter in expanded form, and inserted in the vena cava such that the blood flow, against the filter is the opposite of the blood flow as shown in FIG. 1.

FIG. 3 is an end view of the vena cava filter of the present invention.

FIG. 4 is an enlarged view of the attachment means of the vena cava filter of the present invention.

DESCRIPTION OF THE PREFERRED EMBODIMENT

Figure 5:
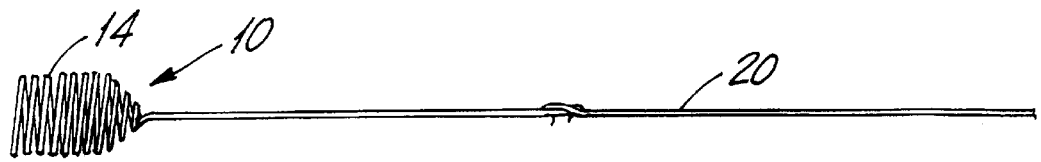
FIG. 5 is a schematic side view, in section, of another embodiment of the vena cava filter showing an elongated removal wire.

Referring now to the drawings the reference numeral 10 generally denotes the vena cava filter of the present invention. As seen in FIGS. 1 and 2 the filter 10 can be placed in the inferior vena cava 12. Filter 10 can be oriented, as shown in FIGS. 1 and 2, in two opposite directions with reference to the flow of blood through the vena cava, the arrows in FIGS. 1 and 2 indicating direction of blood flow.

Vena cava filter 10 is composed of a single, high memory wire 14. Wire 14 has a coiled cylindrical portion 14a and a coiled conical portion 14b. The coils of the cylindrical portion 14b are formed to have a sufficiently large diameter to contact the walls 12a, 12b, of the inferior vena cava. The diameter of the 14b coils, as well as the number of points where the coils contact the vena cava walls cause the coils 14b to act as both a centering and stabilizing device to position and hold the filter appropriately in the vena cava.

Attached to the end of the cylindrical portion 14b is an anchoring means 18. Associated with the end of the conical portion 14a in one embodiment of the invention is removing means 18 to enable the vena cava filter to be easily removed from the body.

Filter 10, is capable of assuming a straight configuration when in a catheter. This aids in delivery of the filter and enables the filter to be placed in the inferior vena cava using a 3, 4, or 5 French Catheter.

The wire 12 must be made of high memory material so that it regains its coiled configuration after it is removed from the catheter. Although the wire may be formed from any high memory material presently preferred materials are nitinol, titanium, stainless steel, an absorbable polymer (such as polylactic acid) or a polymer coated metal. The material from which the wire is mace is intended to be as anti-thrombogenic as possible.

Filter 10 can be easily and safely introduced into the inferior vena cava using a small bore catheter. It can be retrieved easily with a similarly small bore catheter using removing means 18. Alternatively, if the filter is formed of an absorbable polymer removal is not necessary since the filter will be absorbed by the body within twelve to twenty-four months. Since filter 10 can be positioned in either direction it minimizes the possibility of filter motion or obstruction due to a large clot. If filter 10 is positioned with its conical portion 14a facing into the flow of blood it will filter most efficiently as portion 14a will close up as clots impact it. Conversely, if portion 14a faces away or with the flow of blood, it will open up and filter less efficiently as very large clots impact it. This solves the problem encountered with existing filters in that in some patients, where there is a very diffuse deep vein thrombosis, large showers of clot can completely occlude the filter or force the filter out of position. Filter 10 when positioned with portion 14a with the flow prevents large clot from occluding it and disrupting its position. Filter 10 is easy to manufacture and relatively inexpensive.

Preferably, filter 10 is formed of nitinol. The fitter, when in its coiled configuration, has a length of 5 cm. In its uncoiled configuration the filter has a length of about 85 cm. Filter 10 can be introduced using a catheter as small as 3 French. The diameter of the coils of the cylindrical portion are approximately 3 cm. In this preferred embodiment approximately 80% of the length of the filter contacts the walls of the inferior vena cava. In order to properly center and stabilize the filter, coils 14b should contact the vena cava wall over a minimum of three revolutions and preferably should contact the wall at 7 revolutions. Further, for the centering and stabilizing of the filter, the filter should be formed such that the vena cava inner diameter is 0.050–0.75% narrower than the relaxed outer diameter of coils 14b. In the preferred embodiment of the invention anchor 16 is a sharp angled point and retrieving means 18 is a threaded end.

In another embodiment of the inventory shown in FIG. 5, an elongated removal segment 20 is provided in lieu of retrieving means 18. This embodiment of the invention is intended to remain in the body for only a very short period of time (under one week). Elongated segment 20 extends outwardly from the patient's body and is used to remove the filter from the patient. Elongated removal segment 20 in the preferred embodiment is about 90 cm in length. This embodiment may also be used to filter clots in areas other than the vena cava. By way of example the filter can be used in conjunction with lysing means so that clots mechanically and chemically lysed will be trapped by the filter to thus prevent them from potentially becoming distal emboli.

Figure 6:
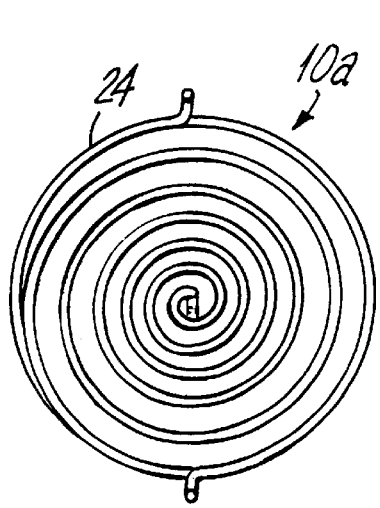
FIG. 6 is a view analogous to FIG. 1 showing another embodiment of the invention.
Figure 7:
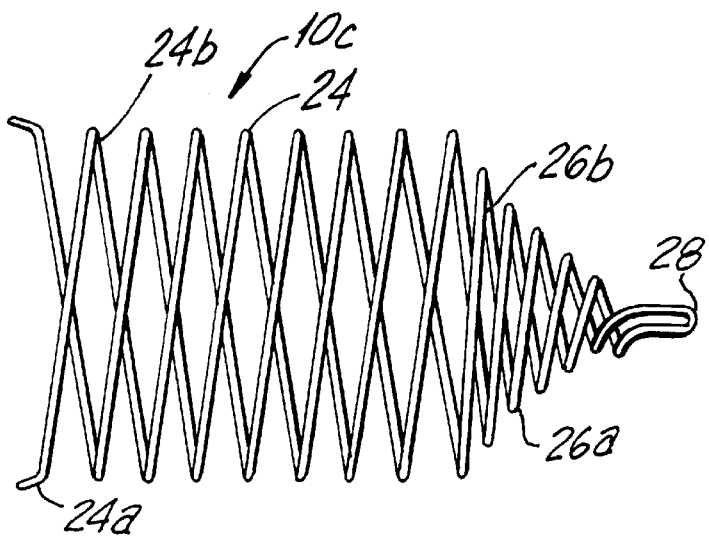
FIG. 7 is a view analogous to FIG. 3 but showing the FIG. 6 embodiment.

FIGS. 6 and 7 show another embodiment of the invention. The reference numbered 10a generally denotes the filter. In this embodiment high memory wire 24 is configured to provide two substantially identical coiled cylindrical portions 24a, 24b and two substantial identical coiled conical portions 26a, 26b. When the filter 10a is in its coiled state the cylindrical portions 24a and 24b substantially overlap one another as do the conical portions 26a, 26b. In this embodiment the retriever means constitutes a loop 28 at the distal end of the filter 10a. Loop 28 is formed by the folding of the high memory wire 24. The provision of two substantially overlying wire segments serves multiple purposes. It makes retrieval easier by providing loop 28 into which a retrieval implement is automatically guided by the overlying coils themselves. Further, it provides extra contact points with the vena cava in less length. It also allows the filter 10a, in its uncoiled state to be shorter than filter 10 in its uncoiled states thus permitting introduction with a shorter catheter. In its preferred embodiment filter 10a has a coiled length of about 5 cm, an uncoiled length of about 42 cm and is introducible using a 5 French catheter.

What is claimed:

1. A non-permanent clot filter formed of a single high memory coiled wire, said coiled wire having a cylindrical segment and a conical segment, said coiled wire assuming a straight configuration when in a catheter, said coiled wire having a first end and a second end, said cylindrical segment extending from said first end to an intermediate position and said conical segment extending from said intermediate position to said second end.

2. The clot filter of claim 1 wherein:

said cylindrical segment has a predetermined diameter and has a sufficient number of turns to center and stabilize said filter within the blood vessel in which it is intended to operate.

3. The clot filter of claim 2 further comprising:

an anchor at said first end of said coiled wire to attach said filter to a blood vessel.

4. The filter of claim 2 wherein said cylindrical segment has a diameter of about three centimeters and wherein about 80 percent of the length of said wire is contained in said cylindrical segment.

5. The filter of claim 3 wherein said anchor is a sharp angled point.

6. The clot filter of claim 1 further comprising:

an anchor at said first end of said coiled wire to attach said filter to a blood vessel.

7. The filter of claim 6 wherein said anchor is a sharp angled point.

8. The filter of claim 1 wherein said filter is made from an absorbable material.

9. The filter of claim 8 wherein said absorbable material is a polylactic acid.

10. The filter of claim 1 wherein said wire is formed of a material selected from the group consisting of: titanium, stainless steel and nitinol.

11. The filter of claim 1 wherein said wire is formed of a polymer coated metal.

12. The filter of claim 1 wherein said wire has a coiled length of about five centimeters and an uncoiled length of about ninety centimeters.

13. The filter of claim 1 wherein said cylindrical segment has a diameter of about three centimeters and wherein about 80 percent of the length of said wire is contained in said cylindrical segment.

* * * * *